(12) United States Patent
Bettencourt-Silva et al.

(10) Patent No.: US 11,942,226 B2
(45) Date of Patent: Mar. 26, 2024

(54) PROVIDING CLINICAL PRACTICAL GUIDELINES

(71) Applicant: INTERNATIONAL BUSINESS MACHINES CORPORATION, Armonk, NY (US)

(72) Inventors: Joao H Bettencourt-Silva, Dublin (IE); Marco Luca Sbodio, Castaheany (IE); Natalia Mulligan, Dublin (IE); Theodora Brisimi, Dublin (IE)

(73) Assignee: International Business Machines Corporation, Armonk, NY (US)

( * ) Notice: Subject to any disclaimer, the term of this patent is extended or adjusted under 35 U.S.C. 154(b) by 182 days.

(21) Appl. No.: 16/660,502

(22) Filed: Oct. 22, 2019

(65) Prior Publication Data
US 2021/0118578 A1    Apr. 22, 2021

(51) Int. Cl.
*G16H 70/20* (2018.01)
*G06N 20/00* (2019.01)
*G16H 10/60* (2018.01)
*G16H 50/30* (2018.01)

(52) U.S. Cl.
CPC ............ *G16H 70/20* (2018.01); *G06N 20/00* (2019.01); *G16H 10/60* (2018.01); *G16H 50/30* (2018.01)

(58) Field of Classification Search
CPC ........ G16H 70/20; G16H 50/30; G16H 10/60; G16H 50/70; G06N 20/00
See application file for complete search history.

(56) References Cited

U.S. PATENT DOCUMENTS

| | | | |
|---|---|---|---|
| 8,020,564 B2 | 9/2011 | Batch | |
| 2005/0214731 A1* | 9/2005 | Smith | G09B 7/00 434/322 |
| 2012/0046966 A1* | 2/2012 | Chang | G16H 50/20 705/3 |
| 2013/0197922 A1 | 8/2013 | Vesto | |
| 2013/0297340 A1 | 11/2013 | Van Zon et al. | |
| 2014/0297324 A1 | 10/2014 | Duftler | |
| 2016/0019352 A1* | 1/2016 | Cohen | G16H 15/00 705/3 |
| 2016/0063212 A1 | 3/2016 | Monier et al. | |
| 2018/0157796 A1* | 6/2018 | Jain | G06F 40/30 |
| 2018/0300640 A1* | 10/2018 | Birnbaum | G16H 10/20 |
| 2020/0082941 A1* | 3/2020 | Wang | G16H 50/20 |
| 2020/0279623 A1* | 9/2020 | Ozeran | G16H 10/40 |
| 2020/0327994 A1* | 10/2020 | Wimberger-Friedl | G16H 50/50 |

OTHER PUBLICATIONS

"OptCare—A system for for personalizing clinical care pathways," Mannarswamy et al., IP.com Disclosure No. IPCOM000244979D, Publication Date: Feb. 4, 2016, (13 Pages).
"Development of Clinical Practice Guidelines." Hollon et al., Annu. Rev. Clin. Psychol. 2014. 10: 213-41, (30 Pages).
(Continued)

*Primary Examiner* — Michael Tomaszewski
*Assistant Examiner* — Shyam M Goswami
(74) *Attorney, Agent, or Firm* — Michael A. Petrocelli

(57) ABSTRACT

Embodiments for providing clinical practice guidelines by a processor. One or more clinical practice guidelines (CPGs) may be automatically generated according for one or more cohorts using evidence data and patient data from one or more data sources.

18 Claims, 8 Drawing Sheets

(56) References Cited

OTHER PUBLICATIONS

"Automatic generation of computable implementation guides from clinical information models Journal of Biomedical Informatics." Bosca et al.,55 (2015) pp. 143-152, (10 Pages).
J. Bittl and Y. He, "Bayesian Analysis: A Practical Approach to Interpret Clinical Trials and Create Clinical Practice Guidelines," Bittl et al., Circ. Cardiovasc. Qual. Outcomes. Aug. 2017; 10(8). pii: e003563. doi: 10.1161/CIRCOUTCOMES.117.003563, (11 Pages).
Bao et al., "Table-to-Text: Describing Table Region with Natural Language", arXiv: 1805.11234v1, May 29, 2018, 9 pages.
Brouwer, "Effect of fish oil on ventricular tachyarrhythmia in three studies in patients with implantable cardioverter defibrillators", European Heart Journal, vol. 30, Issue 7, Apr. 2009, pp. 820-826.
CDC Archive, "Lesson 3: Measures of Risk", Principles of Epidemiology, Lesson 3—Section 5, Accessed on Dec. 21, 2023, 5 pages.
De Backere et al., "Towards Automated generation and execution of clinical guidelines: Engine design and implementation through the ICU Modified Schofield use case", Computers in Biology and Medicine, vol. 42, (2012), pp. 793-805.
Fournier-Viger et al., "Fast Vertical Mining of Sequential Patterns Using Co-occurrence Information", PAKDD 2014, Part I, LNAI 8443, pp. 40-52, 2014.
Jimenez-Candil et al., "Beta-blocker therapy is associated with a lower incidence of syncope due to fast ventricular tachycardias among implantable cardioverter-defibrillator patients with left ventricular dysfunction: results from a multicenter study", Abstract, J. Interv. Card Electrophysiol., Jun. 2018, vol. 52, No. 1, pp. 69-76.
Kiritchenko et al., "ExaCT: automatic extraction of clinical trial characteristics from journal publications", BMC Medical Informatics and Decision Making 2010, 10:56, 17 pages.

Liu et al., "Table-to-text Generation by Structure-aware Seq2seq Learning", arXiv: 1711.09724v1, Nov. 27, 2017, 8 pages.
Martini et al., "Easing the Formalization of Clinical Guidelines with a User-tailored, Extensible Agile Model Driven Development (AMDD)", 21st IEEE International Symposium on Computer-Based Medical Systems, (2008), pp. 120-125.
Medscape, "Clinical Practice Guidelines", Accessed Dec. 21, 2023, 9 pages.
NCBI, "Examples of Practice Guidelines", National Library of Medicine, National Institutes of Health, Institute of Medicine (US) Committee to Advise the Public Health Service on Clinical Practice Guidelines; Field MJ, Lohr KN, editors, Clinical Practice Guidelines: Directions for a New Program. Washington (DC): National Academies Press (US); 1990, 10 pages.
NICE, National Institute for Health and Care Excellence, "Guidance", 2023, 3 pages.
NLM, Unified Medical Language System® (UMLS®), Accessed on Dec. 19, 2023, 3 pages.
Saarel et al., "Safety of Sports for Young Patients With Implantable Cardioverter-Defibrillators", Original Article, Circulation: Arrhythmia and Electrophysiology, Nov. 2018, vol. 11, 9 pages.
Toledo-Ronen et al., "Learning Sentiment Composition from Sentiment Lexicons", Proceedings of the 27th International Conference on Computational Linguistics, pp. 2230-2241, Santa Fe, New Mexico, USA, Aug. 20-26, 2018.
Truran et al., "Automatic generation of limited-depth hyperdocuments from clinical", Conference Paper, Sep. 2013, 5 pages.
Wikipedia, "Recommender system", Accessed on Dec. 22, 23, 14 pages.
Zaki, Spade: An Efficient Algorithm for Mining Frequent Sequences, Machine Learning, 42, pp. 31-60, 2001.

* cited by examiner

|  | OUTCOME IS O | OUTCOME IS NOT O | TOTAL |
|---|---|---|---|
| PATTERN IS P | NUMBER OF PATIENTS WITH PATTERN P AND WITH OUTCOME O (TRUE POSITIVES, TP) | NUMBER OF PATIENTS WITH PATTERN P AND WITHOUT OUTCOME O (FALSE POSITIVES, FP) | TP + FP |
| PATTERN IS NOT P | NUMBER OF PATIENTS WITHOUT PATTERN P AND WITH OUTCOME O (FALSE NEGATIVES, FN) | NUMBER OF PATIENTS WITHOUT PATTERN P AND WITHOUT OUTCOME O (TRUE NEGATIVES, TN) | FN + TN |
| TOTAL | TP + FN | FP + TN | TP + FP + FN + TN |

FIG. 6

| WE FOUND AT LEAST ONE OUTCOME FOR THE PATTERN P | THERE IS AT LEAST ONE ACTIONABLE ELEMENT IN THE PATTERN P | RECOMMENDATION IS |
|---|---|---|
| TRUE | TRUE | IMPERATIVE |
| TRUE | FALSE | DESCRIPTIVE |
| FALSE | TRUE | DESCRIPTIVE |
| FALSE | FALSE | DESCRIPTIVE |

710

| DATA ELEMENT E1 | DATA ELEMENT E12 | DATA ELEMENT E32 | DATA ELEMENT E42 | OUTCOME O |
|---|---|---|---|---|
| ... | <"2013-07-13", TRUE, C0024886, T061> | ... | ... | <"TRUE", "SYNCOPE [C0039070]", "SIGN OR SYMPTOM [T184]"> |

PROVIDING CLINICAL PRACTICAL GUIDELINES

BACKGROUND OF THE INVENTION

Field of the Invention

The present invention relates in general to computing systems, and more particularly to, various embodiments for automatically generating clinical practice guidelines by a processor using structured and unstructured data.

Description of the Related Art

In today's society, consumers, business persons, educators, and others use various computing network systems with increasing frequency in a variety of settings. The advent of computers and networking technologies have made possible the increase in the quality of life while enhancing day-to-day activities. For example, many individuals require extensive use of technology relating to the health and the medical field.

Computing systems can include an Internet of Things (IoT), which is the interconnection of computing devices scattered across the globe using the existing Internet infrastructure. IoT devices may be embedded in a variety of physical devices or products. As great strides and advances in technologies come to fruition, the greater the need to make progress in these systems advantageous for efficiency and safety such as, for example, for using the vast amount of available data to recognize impacts on a well-being or health of a person.

SUMMARY OF THE INVENTION

Various embodiments for providing clinical practice guidelines using one or more processors, are provided. In one embodiment, by way of example only, a method for automatically generating clinical practice guidelines by a processor using structured and unstructured data, again by a processor, is provided. Evidence data and patient data may be analyzed from one or more data sources. One or more clinical practice guidelines (CPGs) may be automatically generated according for one or more cohorts using the evidence data and the patient data from the one or more data sources.

BRIEF DESCRIPTION OF THE DRAWINGS

In order that the advantages of the invention will be readily understood, a more particular description of the invention briefly described above will be rendered by reference to specific embodiments that are illustrated in the appended drawings. Understanding that these drawings depict only typical embodiments of the invention and are not therefore to be considered to be limiting of its scope, the invention will be described and explained with additional specificity and detail through the use of the accompanying drawings, in which:

FIG. 6 is an additional block diagram depicting validation tables used in providing clinical practice guidelines in which aspects of the present invention may be realized;

FIG. 7 is an additional block diagram depicting building recommendations for providing clinical practice guidelines in which aspects of the present invention may be realized.

DETAILED DESCRIPTION OF THE DRAWINGS

Figure 1:
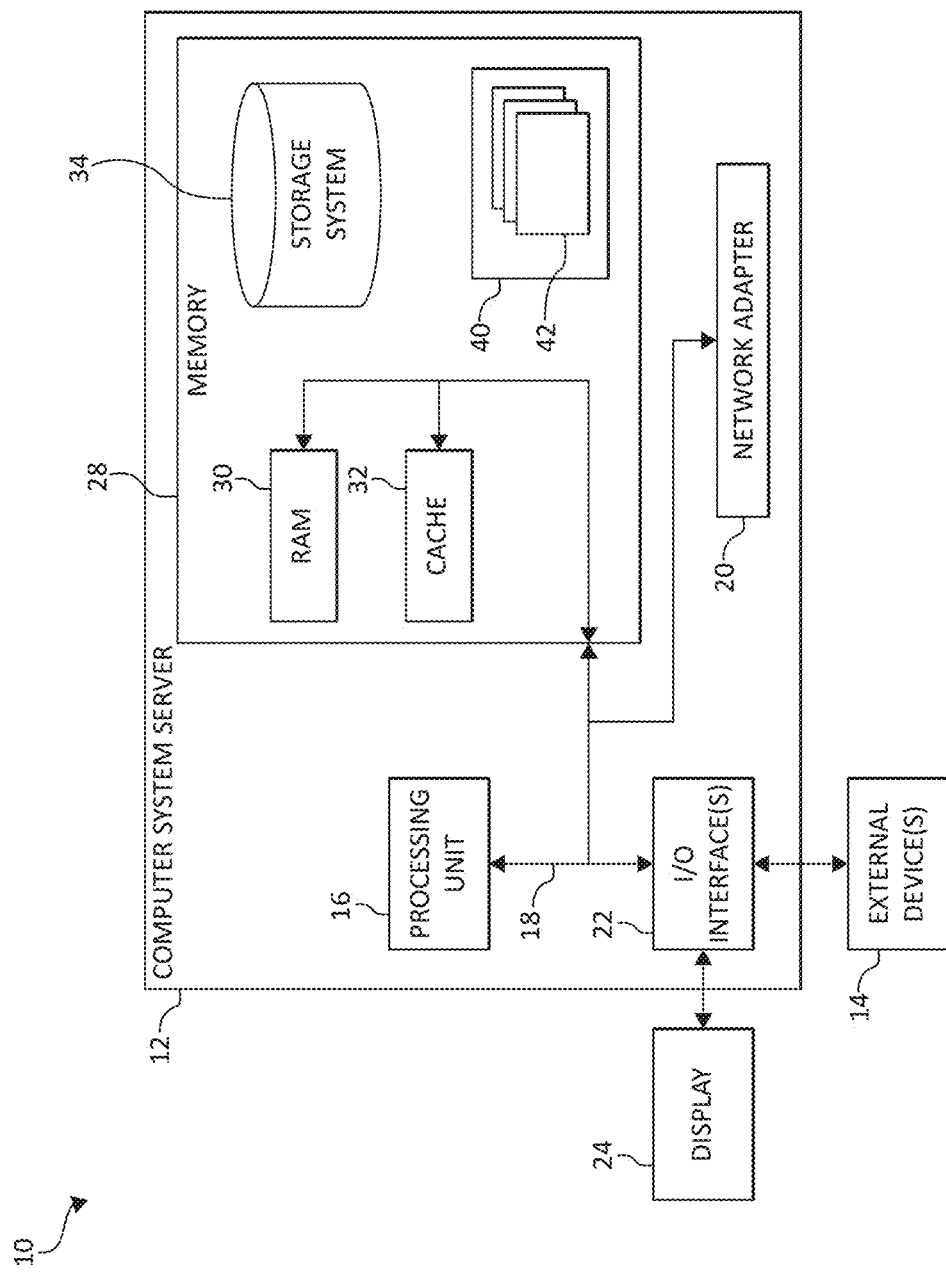
FIG. 1 is a block diagram depicting an exemplary computing node according to an embodiment of the present invention.

As a preliminary matter, computing systems may include large scale computing called "cloud computing," in which resources may interact and/or be accessed via a communication system, such as a computer network. Resources may be software-rendered simulations and/or emulations of computing devices, storage devices, applications, and/or other computer-related devices and/or services run on one or more computing devices, such as a server. For example, a plurality of servers may communicate and/or share information that may expand and/or contract across servers depending on an amount of processing power, storage space, and/or other computing resources needed to accomplish requested tasks. The word "cloud" alludes to the cloud-shaped appearance of a diagram of interconnectivity between computing devices, computer networks, and/or other computer related devices that interact in such an arrangement.

Additionally, the Internet of Things (IoT) is an emerging concept of computing devices that may be embedded in objects, especially appliances, and connected through a network. An IoT network may include one or more IoT devices or "smart devices", which are physical objects such as appliances with computing devices embedded therein. Many of these objects are devices that are independently operable, but they may also be paired with a control system or alternatively a distributed control system such as one running over a cloud computing environment.

The prolific increase in use of IoT appliances in computing systems, particularly within the cloud computing environment, in a variety of settings provide various beneficial uses to a user such as, for example, a medical patient. For example, as the demand for and access to data continues to expand in society, consumers of information content, particularly individuals desiring to make well-informed decisions regarding a medical condition or health state, continue to increase. The openness of the internet with the ever-increasing availability of a variety of types of computing devices, IoT devices, and the cloud computing environment for viewing, interacting, or engaging with information, provides the ability of users to have continuous access to information content relating to a variety of settings.

For example, within the health care industry, clinical practice guidelines ("CPGs") may be used by various types of health professionals. In one aspect, evidence-based health care/medicine and evidence-based policies are approaches in the health care industry. A CPG may be a set of recommendations, actions and goals that support physicians/health care professions making decisions to improve health service delivery and outcomes. In an additional aspect, a CPG may be statements that include recommendations intended to optimize user/patient care that are informed by a systematic review of evidence and an assessment of the benefits and harms of alternative care options. Thus, rather than dictating a one-size-fits-all approach to patient care, a CPG may offer an evaluation of a quality of relevant scientific literature, and an assessment of the likely benefits and harms of a particular treatment. This information enables health care clinicians to select a "best care" or "appropriate care" for a unique patient based on a patient preference.

The CPGs may also include any other evidence-based documents that describe a set of recommendations, instructions or tasks. For example, a local hospital protocol for management of patients with norovirus, a set of recommendations derived from the results of a clinical trial or a research paper with such similar information. A section of a CPG may refer to a particular recommendation or action described in the guideline. A CPG is a collection of multiple recommendations. For example: "measure blood pressure at least once every 12 months" is a recommendation of the Type 2 Diabetes guideline (NICE guideline NG28). It should be noted that as user herein, the "recommendation" may relate to a section of a CPG document (e.g., one or more paragraphs) describing instructions, steps, operations, protocols, and/or tasks intended to optimize patient care (e.g., optimize the health state of a user). Also, one or more aspects of the present invention may apply to any other evidence-based documents that describe a set of recommendations, instructions or tasks. For example, the present invention may recommend for a local hospital protocol for management of patients with a particular illness/sickness, a set of recommendations derived from the results of a clinical trial or perhaps a research paper with such similar information.

As used herein, the terms "Clinical Practice Guidelines," "Clinical Guidelines," "Guidelines," and "Clinical Pathways" may be used interchangeably. It should be noted, as used herein, the term "patient" may be used interchangeably with the terms "user." The patient profile may include a collection of historical data (e.g., electronic data from one or more electronic health care records) that may be related to one or more medical conditions of a user.

Effective CPG may be used, for example, to: 1) reduce disparities in healthcare delivery (e.g., there may be variabilities between regional and provider-level clinical care leading to poor outcomes and added costs that could be avoided by adhering to one or more CPGs, and 2) reduce the burden that health care professionals currently faces to stay current on, and adhere to, the increasing amounts of medical evidence. Adhering to a CPG may improve healthcare in theory, but guidelines may fail to address local constraints and knowledge (e.g., available in electronic health records (EHRs)). In case of a manual identification process, a use-case may include finding the CPGs describing a healthcare/well-being plan that a specific patient is following.

However, developing CPGs is a complex process that involves several domain experts and practitioners. For example in the healthcare domain, some healthcare organizations may provide a manual describing processes and methods to develop a CPG. In so doing, two important steps in the development of a CPG are required such as, for example: 1) identifying the evidence (e.g., evidence-based medicine evidence and/or evidence-based policies): literature searching and evidence submission, and 2) reviewing research evidence.

Accordingly, various embodiments are provided herein for automatically generating clinical practice guidelines. Evidence data and patient data may be analyzed from one or more data sources. One or more clinical practice guidelines (CPGs) may be automatically generated according for one or more cohorts using the evidence data and the patient data from the one or more data sources.

In one aspect, the present invention may automatically generate one or more CPGs from structured and unstructured data thereby introducing a new, more direct, way of creating recommendations and guidelines for given diseases, sickness, illness, or other health related malady, procedures or very specific sets of input variables (e.g., lifestyle factors and behaviors together with certain conditions).

In one aspect, the generated/created clinical practice guidelines may be used to support practitioners in reviewing and improving the results by 1) identifying the evidence: literature searching and evidence submission, and 2) reviewing research evidence by ranking each section of a guideline based on evidence from literature. That is, the process of creating, building, and/or generating one or more CPGs may include identifying and relying on evidence (e.g., clinical trials) carried out independently on specific patient populations.

In one aspect, the development of each CPG does not exploit datasets containing individual-level details of the patients for a specific disease, but rather, relies on assertions made in clinical research publications. Said differently, in one aspect, the present invention generates computer-interpretable guidelines starting from text-based guidelines using machine learning operations (e.g., natural language processing "NLP") as compared to generating guidelines from patient data and evidence data.

In one aspect, one or more data sources may be analyzed for creating, building, and/or generating clinical practice guidelines (CPGs). One or more sections/recommendations of each CPG may be learned, generated, and/or created. A score may be assigned to each of the sections/recommendations of the CPGs, or even the CPGs themselves, according to evidential data identified in one or more data sources and patient data. The one or more of the CPGs may be ranked according to the scoring.

Thus, the present invention generates recommendations in natural language and organizes the recommendations into a CPG. Additionally, the present invention allows user interaction and feedback to achieve consensus on a finalized CPG so as to provide a "complete" picture of possible recommendations based on evidence by presenting all range of outcomes for statistically relevant patterns for the patient cohort selected by some input discriminative variables. It should be noted that the present invention does not require an input patient population segmented based on patient outcomes.

It should be noted that one or more calculations may be performed using various mathematical operations or functions that may involve one or more mathematical operations (e.g., solving differential equations or partial differential equations analytically or computationally, using addition, subtraction, division, multiplication, standard deviations, means, averages, percentages, statistical modeling using statistical distributions, by finding minimums, maximums or similar thresholds for combined variables, etc.).

It should also be noted that as used herein, "health state" may include at least one or more medical conditions, a well-being (e.g., subjective well-being "SWB", emotional well-being, mental well-being, physical well-being, or an overall well-being) of the user/patient, an emotional state of the user/patient, biometric data, behavior patterns, a health profile of the user/patient, or a combination thereof. In one aspect, well-being may be generally described as a normal/standardized or satisfactory condition of existence of the user or a state characterized by health, happiness, emotional stability, mental stability, physical stability, or success. A well-being of a user/patient may be defined.

For example, a knowledge base or ontology may be used to define a well-being for a user/patient and may include defining and/or indicating one or more correlations between a health state, a plurality of states, medical conditions, ADL, and context of daily living (CDL). In an additional aspect, well-being may include the alleviation of adverse impacts upon a person's medical condition, emotional stability, mental stability, physical stability, financial stability, physiological problems, as well as to improve performance in many aspects of life such as daily activities, physical, emotional, mental activities, environmental conditions, and other functions, and also to contribute to the regulation of the various physiological systems of the organism (e.g., person) such as, the immune system. In one aspect, the well-being may be a subjective well-being (SWB) that may be defined as the degree to which people have positive thoughts and feelings about their lives and are often measured through self-reports of life satisfaction. A rating or scaling system may be used. For example, a number system from 1-10 may be used where 10 may indicate the greatest degree of positive thoughts and feelings while a 1 may indicate the least most degree of positive thoughts and feelings. A well-being of a person may be defined, stored, and/or included in a knowledge domain or ontology.

In one aspect, the one or more customized communications further include providing one or more notifications or suggestions to alter current activities of daily living (ADL) of the user, future ADLs of the user, or a combination thereof. As used herein, activities of daily living ("ADL" or "ADLs") may refer to any activities that people perform during a day or other time period. For example, activities of daily living may include many activities that take place throughout the day, particularly going to work, child-care, elderly care, health management, communication management, financial management, safety/emergency responses, shopping, visiting friends or family, traveling, housekeeping, grooming or personal hygiene practices, meal preparation/dining out, engaging in social media, and even using a computer. ADL may also be used in terms of healthcare to refer to the person's daily self-care activities. The context of daily living ("CDL" or "CDLs") may refer to the context in which one or more ADLs are executed or carried out. The CDL may also include one or more dimensions such as, for example, time, location, environment conditions, weather conditions, traffic conditions, and the like. A knowledge domain may provide one or more correlations or relationships between a person's health state and the ADLs and CDLs.

Some ADLs may also be applicable for one or more types of specific events. For example, a person having experienced a recent surgical procedure may require different or altered ADLs for treatment, recovery, or even resuming previously enjoyed ADLs. Each organism (e.g., person) may have different ADLs than other persons. Accordingly, the ADLs for each person may be learned, identified, and analyzed. In one aspect, the ADLs for a person may be learned such as, for example, using machine learning or using a knowledge domain relating to information about the person's activities and behaviors. A machine learning operation may provide a predictive model that may analyze, determine, identify, and/or predict any ADL behavior or activity for the user.

In general, "best," "appropriate," and/or "optimize" may be used herein interchangeable and refer to and/or defined as "maximize," "minimize," or attain one or more specific targets, objectives, goals, or intentions. "Best," "appropriate," and/or "optimize" may also refer to maximizing a benefit to a user (e.g., maximize a health state/patient profile). "Best," "appropriate," and/or "optimize" may also refer to making the most effective or functional use of a situation, opportunity, or resource.

Additionally, "best," "appropriate," and/or "optimize" may need not refer to a best solution or result but may refer to a solution or result that "is good enough" for a particular application, for example. In some implementations, an objective is to suggest a "best" combination of sections of one or more CPGs, but there may be a variety of factors that may result in alternate suggestion of a combination of sections of one or more CPGs yielding better results. Thus, some changes to the variety of factors may result in a jump from one minimum/maximum to another minimum/maximum. In either case, resulting suggestions of a combination of sections of one or more CPGs may be considered "good enough," "substantially optimal," and/or "sufficiently good." Herein, the terms "best," "appropriate," and/or "optimize" may also refer to such results based on minima (or maxima, depending on what parameters are considered in the optimization problem) for suggesting of a combination of sections of CPGs.

In an additional aspect, the terms "optimize" and/or "optimizing" may refer to an operation performed in order to achieve an improved result such as reduced execution costs or increased resource utilization, whether or not the optimum result is actually achieved. Similarly, the term "optimize" may refer to a component for performing such an improvement operation, and the term "optimized" may be used to describe the result of such an improvement operation.

As used herein, so-called "appropriateness" or "inappropriateness" of sections of one or more CPGs associated with a current patient pathway may be subjective and context dependent. For example, one solution for an appropriate combination of sections of one or more CPGs associated with a current patient pathway may be interpreted and evaluated to be either satisfactory or unsatisfactory depending on one or more contextual factors. Accordingly, the so-called "appropriateness" of a particular combination of sections of one or more CPGs associated with a current patient pathway may depend greatly upon contextual factors, such as a patient profile (e.g., a user profile may include a collection of settings and/or information or attributes with a user such as, for example, gender, weight, age, etc.), environmental factors, social factors, religious factors, cultural factors, and other contextual factors. A deeper, cognitive analysis of the user and CPGs associated with a current patient pathway may be provided to further understand the user and/or interpret the appropriate combination of sections of one or more CPGs associated with a current patient pathway.

It should be noted that reference to calculating an 'interpreted appropriateness" against a predetermined threshold herein following may refer to implementations of a wide variety of metric analysis, data analytics, and other data processing as one of ordinary skill in the art will appreciate. For example, a predetermined threshold may be set as a numerical value, where certain kinds of sections of one or more CPGs associated with a current patient pathway are given certain weighted values, and an aggregate number of the weighted values may be compared against a numerical threshold value.

It should be noted as described herein, the term "cognitive" (or "cognition") may be relating to, being, or involving conscious intellectual activity such as, for example, thinking, reasoning, or remembering, that may be performed using a machine learning. In an additional aspect, cognitive or "cognition may be the mental process of knowing, including aspects such as awareness, perception, reasoning and judgment. A machine learning system may use artificial reasoning to interpret data from one or more data sources (e.g., sensor-based devices or other computing systems) and learn topics, concepts, and/or processes that may be determined and/or derived by machine learning.

In an additional aspect, cognitive or "cognition" may refer to a mental action or process of acquiring knowledge and understanding through thought, experience, and one or more senses using machine learning (which may include using sensor-based devices or other computing systems that include audio or video devices). Cognitive may also refer to identifying patterns of behavior, leading to a "learning" of one or more events, operations, or processes. Thus, the cognitive model may, over time, develop semantic labels to apply to observed behavior and use a knowledge domain or ontology to store the learned observed behavior. In one embodiment, the system provides for progressive levels of complexity in what may be learned from the one or more events, operations, or processes.

In additional aspect, the term cognitive may refer to a cognitive system. The cognitive system may be a specialized computer system, or set of computer systems, configured with hardware and/or software logic (in combination with hardware logic upon which the software executes) to emulate human cognitive functions. These cognitive systems apply human-like characteristics to convey and manipulate ideas which, when combined with the inherent strengths of digital computing, can solve problems with a high degree of accuracy (e.g., within a defined percentage range or above an accuracy threshold) and resilience on a large scale. A cognitive system may perform one or more computer-implemented cognitive operations that approximate a human thought process while enabling a user or a computing system to interact in a more natural manner. A cognitive system may comprise artificial intelligence logic, such as natural language processing (NLP) based logic, for example, and machine learning logic, which may be provided as specialized hardware, software executed on hardware, or any combination of specialized hardware and software executed on hardware. The logic of the cognitive system may implement the cognitive operation(s), examples of which include, but are not limited to, question answering, identification of related concepts within different portions of content in a corpus, and intelligent search algorithms, such as Internet web page searches.

In general, such cognitive systems are able to perform the following functions: 1) Navigate the complexities of human language and understanding; 2) Ingest and process vast amounts of structured and unstructured data; 3) Generate and evaluate hypotheses; 4) Weigh and evaluate responses that are based only on relevant evidence; 5) Provide situation-specific advice, insights, estimations, determinations, evaluations, calculations, and guidance; 6) Improve knowledge and learn with each iteration and interaction through machine learning processes; 7) Enable decision making at the point of impact (contextual guidance); 8) Scale in proportion to a task, process, or operation; 9) Extend and magnify human expertise and cognition; 10) Identify resonating, human-like attributes and traits from natural language; 11) Deduce various language specific or agnostic attributes from natural language; 12) Memorize and recall relevant data points (images, text, voice) (e.g., a high degree of relevant recollection from data points (images, text, voice) (memorization and recall)); and/or 13) Predict and sense with situational awareness operations that mimic human cognition based on experiences.

Other examples of various aspects of the illustrated embodiments, and corresponding benefits, will be described further herein.

It is understood in advance that although this disclosure includes a detailed description on cloud computing, implementation of the teachings recited herein are not limited to a cloud computing environment and/or computing systems associated with one or more vehicles. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported providing transparency for both the provider and consumer of the utilized service.

Service Models are as follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure comprising a network of interconnected nodes.

Referring now to FIG. 1, a schematic of an example of a cloud computing node is shown. Cloud computing node 10 is only one example of a suitable cloud computing node and is not intended to suggest any limitation as to the scope of use or functionality of embodiments of the invention described herein. Regardless, cloud computing node 10 is capable of being implemented and/or performing any of the functionality set forth hereinabove.

In cloud computing node 10 there is a computer system/server 12, which is operational with numerous other general purpose or special purpose computing system environments or configurations. Examples of well-known computing systems, environments, and/or configurations that may be suitable for use with computer system/server 12 include, but are not limited to, personal computer systems, server computer systems, thin clients, thick clients, hand-held or laptop devices, multiprocessor systems, microprocessor-based systems, set top boxes, programmable consumer electronics, network PCs, minicomputer systems, mainframe computer systems, and distributed cloud computing environments that include any of the above systems or devices, and the like.

Computer system/server 12 may be described in the general context of computer system-executable instructions, such as program modules, being executed by a computer system. Generally, program modules may include routines, programs, objects, components, logic, data structures, and so on that perform particular tasks or implement particular abstract data types. Computer system/server 12 may be practiced in distributed cloud computing environments where tasks are performed by remote processing devices that are linked through a communications network. In a distributed cloud computing environment, program modules may be located in both local and remote computer system storage media including memory storage devices.

As shown in FIG. 1, computer system/server 12 in cloud computing node 10 is shown in the form of a general-purpose computing device. The components of computer system/server 12 may include, but are not limited to, one or more processors or processing units 16, a system memory 28, and a bus 18 that couples various system components including system memory 28 to processor 16.

Bus 18 represents one or more of any of several types of bus structures, including a memory bus or memory controller, a peripheral bus, an accelerated graphics port, and a processor or local bus using any of a variety of bus architectures. By way of example, and not limitation, such architectures include Industry Standard Architecture (ISA) bus, Micro Channel Architecture (MCA) bus, Enhanced ISA (EISA) bus, Video Electronics Standards Association (VESA) local bus, and Peripheral Component Interconnects (PCI) bus.

Computer system/server 12 typically includes a variety of computer system readable media. Such media may be any available media that is accessible by computer system/server 12, and it includes both volatile and non-volatile media, removable and non-removable media.

System memory 28 can include computer system readable media in the form of volatile memory, such as random-access memory (RAM) 30 and/or cache memory 32. Computer system/server 12 may further include other removable/non-removable, volatile/non-volatile computer system storage media. By way of example only, storage system 34 can be provided for reading from and writing to a non-removable, non-volatile magnetic media (not shown and typically called a "hard drive"). Although not shown, a magnetic disk drive for reading from and writing to a removable, non-volatile magnetic disk (e.g., a "floppy disk"), and an optical disk drive for reading from or writing to a removable, non-volatile optical disk such as a CD-ROM, DVD-ROM or other optical media can be provided. In such instances, each can be connected to bus 18 by one or more data media interfaces. As will be further depicted and described below, system memory 28 may include at least one program product having a set (e.g., at least one) of program modules that are configured to carry out the functions of embodiments of the invention.

Program/utility 40, having a set (at least one) of program modules 42, may be stored in system memory 28 by way of example, and not limitation, as well as an operating system, one or more application programs, other program modules, and program data. Each of the operating system, one or more application programs, other program modules, and program data or some combination thereof, may include an implementation of a networking environment. Program modules 42 generally carry out the functions and/or methodologies of embodiments of the invention as described herein.

Computer system/server 12 may also communicate with one or more external devices 14 such as a keyboard, a pointing device, a display 24, etc.; one or more devices that enable a user to interact with computer system/server 12; and/or any devices (e.g., network card, modem, etc.) that enable computer system/server 12 to communicate with one or more other computing devices. Such communication can occur via Input/Output (I/O) interfaces 22. Still yet, computer system/server 12 can communicate with one or more networks such as a local area network (LAN), a general wide area network (WAN), and/or a public network (e.g., the Internet) via network adapter 20. As depicted, network adapter 20 communicates with the other components of computer system/server 12 via bus 18. It should be understood that although not shown, other hardware and/or software components could be used in conjunction with computer system/server 12. Examples, include, but are not limited to: microcode, device drivers, redundant processing units, external disk drive arrays, RAID systems, tape drives, and data archival storage systems, etc.

Figure 2:
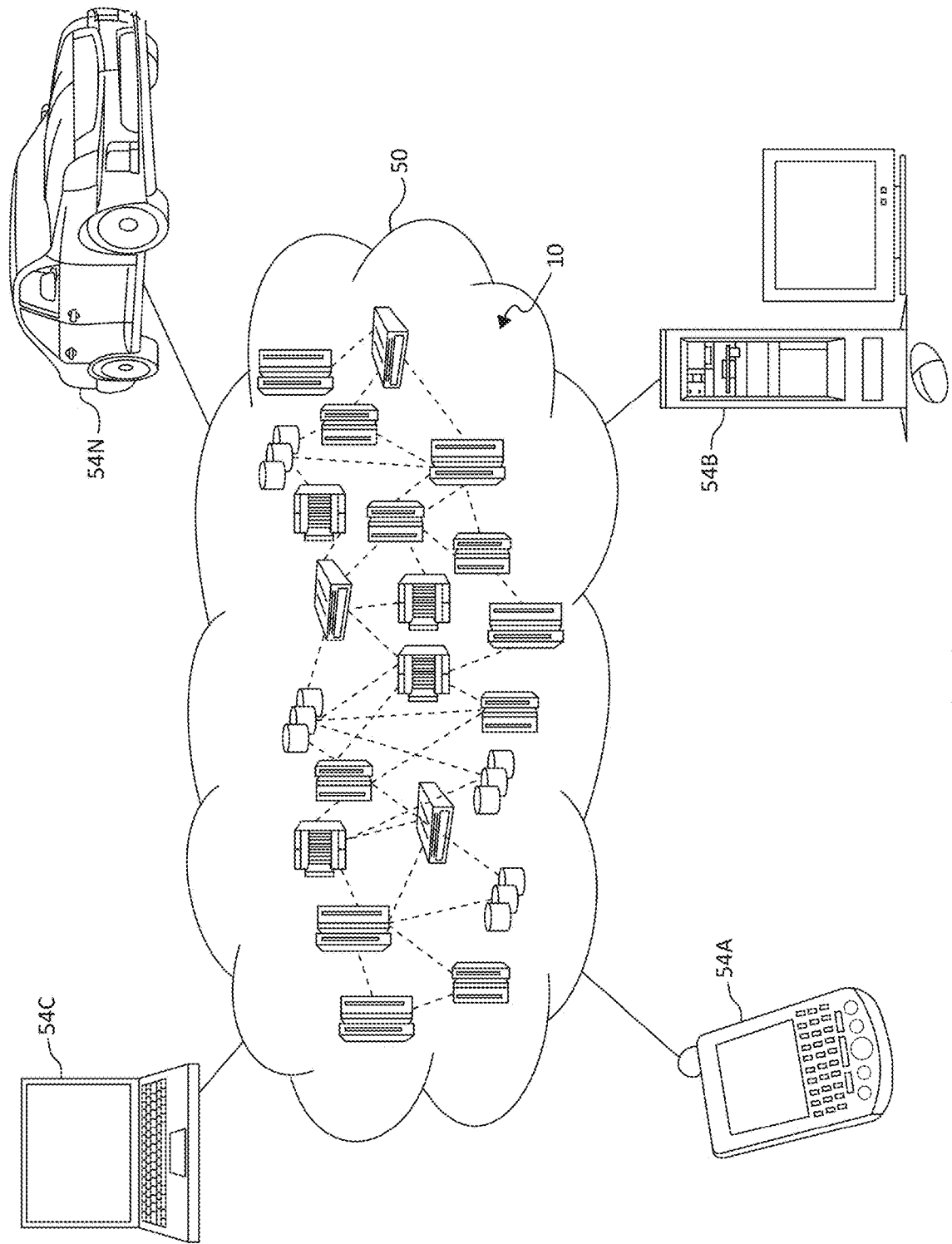
FIG. 2 is an additional block diagram depicting an exemplary cloud computing environment according to an embodiment of the present invention.

Referring now to FIG. 2, illustrative cloud computing environment 50 is depicted. As shown, cloud computing environment 50 comprises one or more cloud computing nodes 10 with which local computing devices used by cloud consumers, such as, for example, personal digital assistant (PDA) or cellular telephone 54A, desktop computer 54B, laptop computer 54C, and/or automobile computer system 54N may communicate. Nodes 10 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 2 are intended to be illustrative only and that computing nodes 10 and cloud computing environment 50 can communicate with any type of computerized device over any type of network and/or network addressable connection (e.g., using a web browser).

Figure 3:
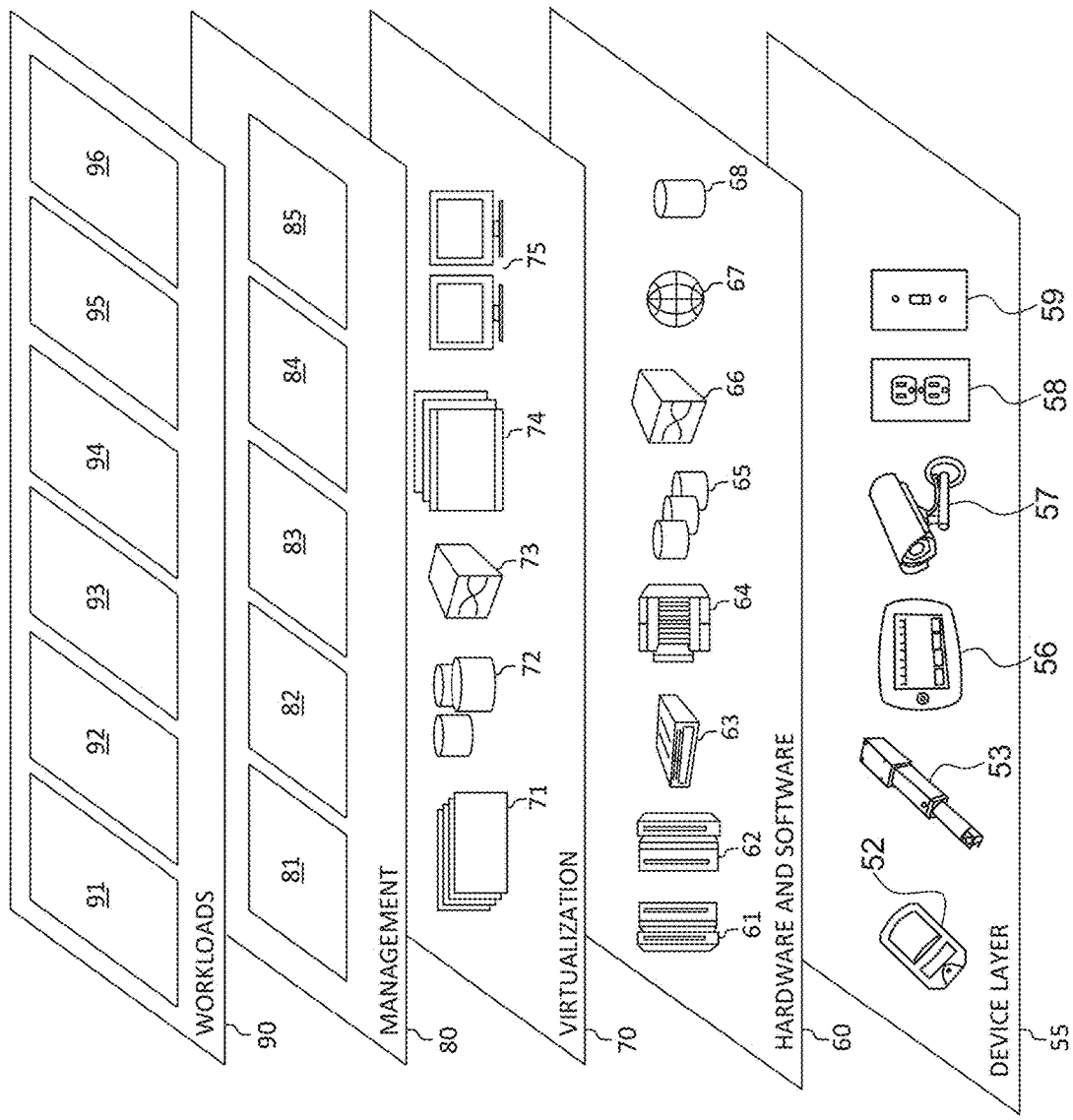
FIG. 3 is an additional block diagram depicting abstraction model layers according to an embodiment of the present invention.

Referring now to FIG. 3, a set of functional abstraction layers provided by cloud computing environment 50 (FIG. 2) is shown. It should be understood in advance that the components, layers, and functions shown in FIG. 3 are intended to be illustrative only and embodiments of the invention are not limited thereto. As depicted, the following layers and corresponding functions are provided:

Device layer 55 includes physical and/or virtual devices, embedded with and/or standalone electronics, sensors, actuators, and other objects to perform various tasks in a cloud computing environment 50. Each of the devices in the device layer 55 incorporates networking capability to other functional abstraction layers such that information obtained from the devices may be provided thereto, and/or information from the other abstraction layers may be provided to the devices. In one embodiment, the various devices inclusive of the device layer 55 may incorporate a network of entities collectively known as the "internet of things" (IoT). Such a network of entities allows for intercommunication, collection, and dissemination of data to accomplish a great variety of purposes, as one of ordinary skill in the art will appreciate.

Device layer 55 as shown includes sensor 52, actuator 53, "learning" thermostat 56 with integrated processing, sensor, and networking electronics, camera 57, controllable household outlet/receptacle 58, and controllable electrical switch 59 as shown. Other possible devices may include, but are not limited to various additional sensor devices, networking devices, electronics devices (such as a remote-control device), additional actuator devices, so called "smart" appliances and a wide variety of other possible interconnected objects.

Hardware and software layer 60 may include hardware and software components. Examples of hardware components include: mainframes 61; RISC (Reduced Instruction Set Computer) architecture-based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provides cost tracking as resources are utilized within the cloud computing environment, and billing or invoicing for consumption of these resources. In one example, these resources may comprise application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provides pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and, in the context of the illustrated embodiments of the present invention, various workloads and functions 96 for automatically generating CPGs. In addition, workloads and functions 96 for automatically generating CPGs may include such operations as data analytics, data analysis, and as will be further described, notification functionality. One of ordinary skill in the art will appreciate that the workloads and functions 96 for automatically generating CPGs may also work in conjunction with other portions of the various abstractions layers, such as those in hardware and software 60, virtualization 70, management 80, and other workloads 90 (such as data analytics processing 94, for example) to accomplish the various purposes of the illustrated embodiments of the present invention.

As previously mentioned, the mechanisms of the illustrated embodiments provide novel approaches for automatically generating clinical practice guidelines using one or more processors. Evidence data and patient data may be analyzed from one or more data sources. One or more clinical practice guidelines (CPGs) may be automatically generated according for one or more cohorts using the evidence data and the patient data from the one or more data sources (e.g., structured data and/or unstructured data). For example, the present invention may provide CPGs in the following steps.

In step 1, one or more algorithms may be minded to extract statistically relevant sequences/patterns from patient data and retaining only those statistically relevant sequences/patterns that contains values of interest (e.g., "cohort selection") as specified by a domain expert. The patient data may include, for example, medical data, lifestyle and behavioral data, social media data, etc.

In step 2, a structured database of evidence (e.g., clinical trials) may be used to identify and/or find outcomes for the sequences computed in step 1.

In step 3, imperative and descriptive CPG recommendations may be produced. An imperative recommendation may suggest one or more actions for the patient and has an associated outcome. A descriptive recommendation may not suggest actions nor have an associated outcome. In one aspect, an imperative recommendation suggests an action for the patient/care worker (e.g., "in order to avoid syncope offer Beta-blocker therapy for patients with ventricular arrhythmia in patients with pacemakers"), whereas a descriptive recommendation illustrates facts relevant for the patient (e.g., "with a probability of 80%, diet intake of omega-3 polyunsaturated fatty acids has no effect in ventricular arrhythmia in patients with pacemakers").

In step 4, for each of the recommendations produced in step 3, one or more validation tables may be generated to ascertain that the results that are statistically significant with respect to the input patient data.

In step 5, each of the recommendations may be ranked based on an assigned, determined, or computed confidence score.

In step 6, the produced recommendations, along with the corresponding confidence, related evidence (if available), and validation table may be displayed on a graphical user interface ("GUI") to enable a domain expert to view and provide adjustments, feedback, and/or analysis.

In step 7, feedback data may be collected and retrieved from a domain expert and the feedback may be used to determine a consensus between domain experts on the generated recommendations. When consensus is reached, the generated recommendations are finalized into a CPG.

Figure 4:
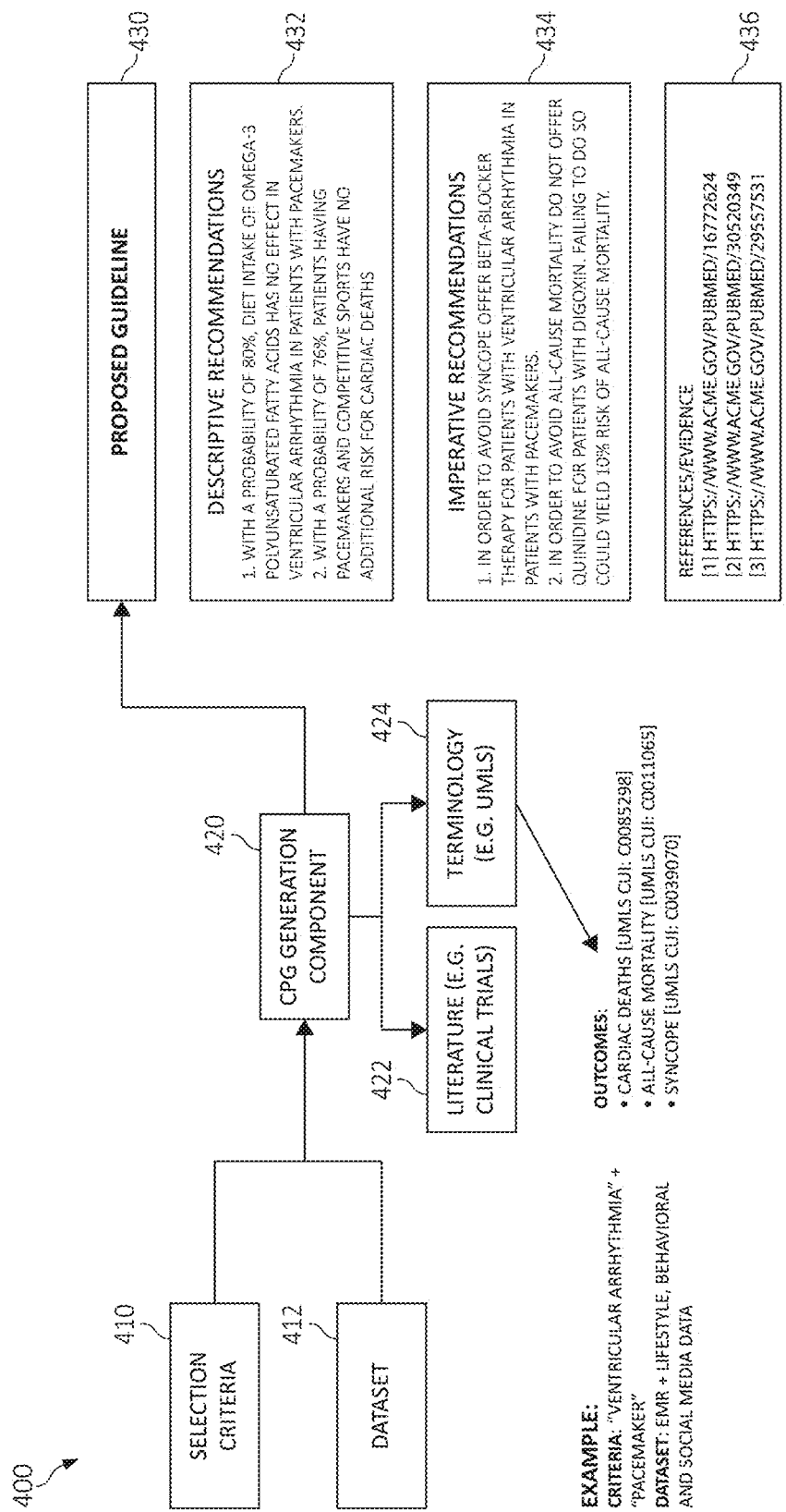
FIG. 4 is an additional block diagram depicting an exemplary functional relationship between various aspects of the present invention.

Turning now to FIG. 4, a block diagram depicting exemplary functionality 500 relating to generating CPGs is depicted, for use in the overall context of providing, creating, and/or generating CPGs workloads and functions and training of a machine-learning model in a computing environment. As shown, the various blocks of functionality are depicted with arrows designating the blocks' 400 relationships with each other and to show process flow. Additionally, descriptive information is also seen relating each of the functional blocks 400. As will be seen, many of the functional blocks may also be considered "modules" of functionality, in the same descriptive sense as has been previously described in FIGS. 1-3. With the foregoing in mind, the module blocks 400 may also be incorporated into various hardware and software components of a system for image enhancement in accordance with the present invention. Many of the functional blocks 400 may execute as background processes on various components, either in distributed computing components, or on the user device, or elsewhere.

That is, the functional components 400 are directed at producing one or more CPG based on pre-existing patient-level data and evidence (e.g., literature based evidence). For example, in one aspect, one or more of the functional blocks 400 provided by one or more of the "modules" or "components" of functionality of FIGS. 1-3, may be virtualized computing services (i.e., virtualized computing, virtualized storage, virtualized networking, etc.). More specifically, one or more of the functional blocks 400 may be virtualized computing, virtualized storage, virtualized networking and other virtualized services that are executing on a hardware substrate.

Starting with blocks 410 and 410, selection criteria data and a dataset may be provided to an intelligent CPG generation component 420. For example, the criteria may be data relating to a selected health related criteria such as, for example, "ventricular arrhythmia" and "pacemaker." The dataset may include, for example, the patient data health data for a user, such as, for example, social network data, physical conditions of the user, activities of daily living (ADL) and associated context of daily living (CDL) of the patient, or a combination thereof.

In blocks 422 and 424, the intelligent CPG generation component 420 may access various terminology (e.g., unified medical language system "UMLS") and various data sources (e.g., literature such as, for example, clinical trials) to learn various outcomes related to the selection criteria and dataset of blocks 410 and 412. For example, the various learned outcomes may include cardiac outcomes, all-cause mortality, syncope.

Thus, the intelligent CPG generation component 420 using the selection criteria and dataset of blocks 410 and 412 and the terminology 422 and data sources 424 may generated one or more proposed CPGs ("guidelines), as in block 4230. The one or more proposed CPGs may include both descriptive recommendations 432, imperative recommendations 434, and/or references/evidence 436 (which may be references and/or evidence supporting or justifying the CPG).

For example, the descriptive recommendations 432 may include one or more recommendations for the selection criteria and dataset of blocks 410 and 412 and the terminology 422 and data sources 424, 1) with an probability of 80%, diet intake of omega-3 polyunsaturated fatty acids may have no effect in ventricular arrhythmia in patients with pacemakers, and/or 2) with a probability of 76%, patients having pacemakers and playing competitive sports have no additional risk for cardiac deaths.

As an additional example, the imperative recommendations 434 may include, for example, 1) in order to avoid syncope, offer beta-blocker therapy for patients with ventricular arrhythmia in patients with pacemakers, and/or 2) in order to avoid all-cause mortality do not offer Quinidine for patients with digoxin. Failing to do so could yield 10% increased risk of all-cause mortality.

Figure 5:
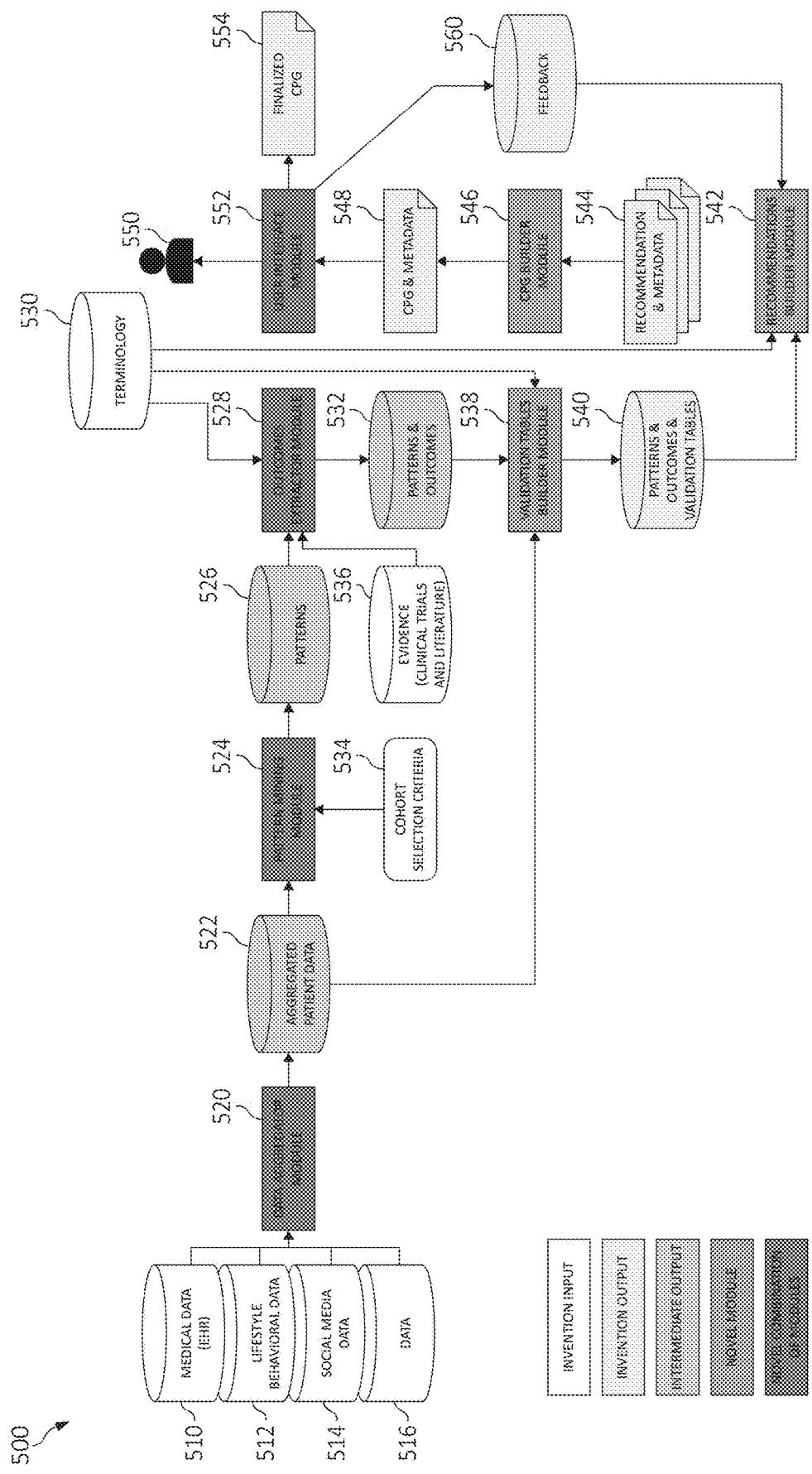
FIG. 5 is an additional block diagram depicting operations for automatically generating clinical practice guidelines in which aspects of the present invention may be realized.

Turning now to FIG. 5, a block diagram depicting exemplary functional components 500 for providing clinical practice guidelines is depicted. FIG. 5 illustrates providing clinical practice guidelines workloads, according to an example of the present technology. As will be seen, many of the functional blocks may also be considered "modules" or "components" of functionality, in the same descriptive sense as has been previously described in FIGS. 1-4. Repetitive description of like elements, components, modules, services, applications, blocks and/or functions employed in other embodiments described herein is omitted for sake of brevity.

As illustrated in FIG. 5, a data aggregator module 520 may aggregate data from various input data sources such as, for example, medical data (e.g., electronic health record "EHR") 510, lifestyle and behavioral data 512 (e.g., data collected by one or more IoT devices such as, for example, a smart phone and/or wearable activity trackers, etc.), social network/media data 514 (e.g., data from a patient's timeline on a social media network), and/or other data such as, for example, activities of daily living (ADL) and associated context of daily living (CDL) of the patient. The data aggregator module 520 may also use terminology (e.g., UMLS) to associate to each data element some semantic information (e.g., concept and semantic type information).

In one aspect, the data aggregator module 520 may use customized Extract, Transform and Load ("ETL") processes. Additionally, in one embodiment, the ETL processes may use operations to semantically enrich the data using the input terminology.

The output of the data aggregator module 520 is provided as aggregated patient data 522, which consists of various data elements. Each data element is associated with a patient, and it consists of a tuple which may include, for example, one or more of the following items: 1) a "timestamp" (can be null) that identifies the point in time (date/time) when this data element happened, 2) an "element-value" that is the actual value of the data element, 3) a "concept-identifier" that is the identifier of a semantic concept associated to the data element, 4) a "semantic-type-identifier" that is the identifier of the semantic type associated to the data element, and 5) the concept-identifier and the semantic-type-identifier may be extracted from the input terminology (e.g., UMLS). To further illustrate, the following is an example of data element (e.g., "e12") when the input terminology is UMLS: e12 equal to or less than the time stamp of "2013-07-13" and where the value "C0024886" is a UMLS code for a specific disease and "T061" is its semantic type ("Therapeutic or preventive procedure").

A pattern mining module 524 may receive as input a set of cohort selection criteria 534. In one aspect, the cohort selection criteria 534 may be specified by a domain expert (e.g., a subject matter expert "SME"), and comprised of a set of pairs (e.g., each pair is of the form <variable, value> and represents a selection criteria), that are used to filter the aggregated patient data 522 to select a cohort. The pattern mining module 24 may extract statistically relevant patterns 526 from the aggregated patient data 522 in the cohort identified by the selection criteria 534. In one aspect, the pattern mining module 24 may use sequential pattern mining operations such as, for example, "SPADE" or its more recent variant. Each pattern (e.g., each of the statistically relevant patterns 526) may be associated to a confidence score (e.g., "Cpattern" that may be normalized in the range [0,1], which may be a support value returned by the pattern mining operation). The output of the statistically relevant patterns 526 comprises the statistically relevant patterns 526. Each of the statistically relevant patterns 526 may include one or more data elements from the aggregated patient data 522. To further illustrate, the following is an example of a pattern p=<e1, e12, e32, e42>, where, for example the data element e12 is the tuple (as described above for the data aggregator module 520).

An outcomes extractor module 528 may receive, as input, the statistically relevant patterns 526 produced by the pattern mining module 524 and uses the statistically relevant patterns 526 to query an evidence database 536 (e.g., one or more data sources such as, for examples, clinical trials/results and medical literature). In one aspect, the outcomes extractor module 528 may use one or more extraction operations. Each outcome consists of a tuple "0" where "0" is equal to =<outcome-value, concept-identifier, semantic-type identifier> where the "outcome-value" is the actual value of the outcome, the "concept-identifier" is the identifier of the semantic concept associated to the outcome, the "semantic-type-identifier" is the identifier of the semantic type associated to the outcome such as, for example, the patterns and outcomes 532. The concept-identifier and the semantic-type-identifier may be extracted from the input terminology 530 (e.g., UMLS).

To further illustrate, the following is an example of an outcome when the input terminology is UMLS and the tuple "0" is equal to <'true', 'Syncope [C0039070]', "Sign or Symptom [T184]'>. Each extracted outcome (e.g., patterns and outcomes 532) may be associated to/with a confidence score (e.g., "Coutcome") and normalized in a range [0, 1], by way of example only. The output of this module consists of an enriched version of the statistically relevant patterns 526 (e.g., enriched patterns and outcomes 532) produced by the pattern mining module 524, where each pattern (of the enriched patterns and outcomes 532) may have zero or more outcomes associated to it. Each pair (of the enriched patterns and outcomes 532) may be associated to a confidence score (e.g., "$C_{<pattern,outcome>}$,") and normalized in the range [0,1], by way of example only. In one aspect, the $C_{<pattern,outcome>}$ may be equal to the following equation:

$$C_{<pattern,outcome>} = C_{pattern} * C_{outcome} \qquad (1).$$

A validation table builder module 538 may build one or more validation tables such as, for example, the validation table 600 depicted in FIG. 6 for a given pattern "p" with an outcome "o". The validation tables (e.g., patterns, outcomes and validation tables 540) such as, for example, the validation table 600 depicted in FIG. 6 may be used to ascertain that the results are statistically significant with respect to the selected cohort in the aggregated patient data 522.

For example, the validation table builder module 538 may build a confusion matrix (e.g., the validation table 600 depicted in FIG. 6), depicting the results of the pattern is "p" and the outcome is "o" indicates that a number of patients with pattern "p" and outcome "o" is true positives ("TP"). The results of the pattern is not "p" and the outcome is "o" indicates that a number of patients without pattern "p" and outcome "o" is false negatives ("TP"). The results of the pattern is "p" and the outcome is not "o" indicates that a number of patients with pattern "p" and without outcome "o" is false positives ("FP"). The results of the pattern is not "p" and the outcome is not "o" indicates that a number of patients without pattern "p" and without outcome "o" is true negatives ("TN").

In one aspect, the concept-identifier and the semantic-type-identifier of the outcome "o" maybe be used to identify a data element $e_o$ in the aggregated patient data 522 having the same concept-identifier. If the input terminology gives a hierarchy of concepts, the present invention may use data elements in the aggregated patient data 522 having a concept-identifier that is a parent of the concept-identifier of the outcome o. The confusion matrix (e.g., the validation table 600) may be filled in/completed by determining/counting how many patients have (or have not) the pattern p and also have (or have not) a data element with concept-identifier $e_o$. In an additional aspect, one or more confidence scores determined/calculated from the validation table 600 may be used to indicate a degree of certainty in a particular outcome. To further illustrate, examples of the confidence scores include a risk/odds ratio and p-values that may be determined.

A recommendations builder module 542 may receive as input a pattern p, its outcome o, and the corresponding validation table (including its confidence scores) (e.g., patterns, outcomes and validation tables 540) and produces a recommendation (which may be produced via a natural langue processing "NLP" operation to be produced in natural language such as, for example, text data). The original pattern p, outcome o, and validation table 600 are associated to the recommendation as metadata such as, for example, recommendation and metadata 544.

In one aspect, a template may be used to produce an imperative recommendation or a descriptive recommendation to respectively produce an imperative CPG recommendation or descriptive CPG recommendation. Additionally, the imperative templates may be associated with one or more desirable and/or undesirable outcomes.

To further illustrate, the following is an example of templates. For example, in a first template, "Template T1" may be an imperative recommendation with desirable outcome "in order to achieve <outcome> offer <X> for patients with <conditions>. Doing so may yield to in addition to <outcome>. [metadata]"

In a second template, "Template T2" may be an imperative recommendation with undesirable outcome: "In order to avoid <outcome> do not offer <X> for patients with <conditions>. Failing to do so could yield to in addition to <outcome>. [metadata]"

In a third template, "Template T3" may be descriptive recommendation "with a probability <P> %, patients with <W> also have <Z>. [metadata]."

Also, in the example templates the variables X, <conditions> Y, W, Z may be populated from values extracted from the patterns using extraction rules. For example, if patent "p" is a sequence than <X> contains all actionable elements in "p", <conditions> value may be defined as all the data elements in "p" before <X>, <Y> may include of all data elements in p after <X>, <P>: $f(C_{pattern})$ where f is a function transforming the confidence of the pattern "p" into a probability. In one aspect, $f(C_{pattern})$ is a percentage of the patients (in the selected cohort) whose data contains a given pattern, <W> is the prefix of the sequence of (all of the elements in "p" except the last element), and <Z> is a last element of the sequence.

In one aspect, the data elements may be classified in the pattern (e.g., the patterns and outcomes 532) as either actionable or observable based on their semantic-type-identifier. Such a classification can be part of the input terminology 530 or learned via a machine learning operation. In one aspect, if a pair <pattern, outcome> generates an imperative or descriptive recommendation, table 710 of FIG. 7 may be used to determine/decide between imperative and descriptive recommendations.

For example, for imperative recommendations, the present invention may determine/decide between a desirable and undesirable recommendation using an NLP operation to classify the outcome of the pair as either desirable or undesirable. A confidence score $C_{<NLp>}$ may be generated. The present invention may also generate a final confidence $C_{recommendation}$ of a recommendation. For descriptive recommendations the $C_{recommendation}$ may be equal to $C_{<pattern,outcome>}$, if there is no associated outcome then Crecommendation=$C_{<pattern>}$.

For imperative recommendations, if the p-value is greater than or equal to (">=") 0.05 from a corresponding validation table then the recommendation a may be dropped/ignored as it is statistically insignificant. Otherwise, the present invention may calculate a composite score G based on $C_{<NLP}$.

$C_{<pattern, outcome>}$, and the OR (risk/odds ratio) derived from the corresponding validation table such as, for example, in the following equation:

$$G = C_{(pattern, outcome)} * C_{(NLP)} * 8\left(\frac{OR}{1-OR}\right). \quad (2)$$

where (OR/(1−OR)) is a probability value between [0,1]. Finally, in one aspect, one or more sentences generated from the templates may be enriched with additional text to transform a table into text. For example, consider the pattern "p" and its outcome "o" as a table with fields/values. For example for pattern p may be equal to or less than ("=<") <e1, e12, e32, e42>, with e12 being equal to <"2013-07-13", true, C0024886, T061>, and outcome <'True', 'Syncope [C0039070]', 'Sign or Symptom [T184]'>, may produce the table 720 of FIG. 7.

Returning to FIG. 5, A CPG builder module 546 may receive as input a collection of recommendations and metadata 544 (e.g., each recommendation associated with metadata), and organize the recommendations and metadata 544 into a CPG document. That is, the output of the CPG builder module 546 may be one or more CPGs and metadata (e.g., CPG and metadata 548). In one aspect, the CPG builder module 546 uses a template of CPG document structured as having 1) an opening section, 2) a body section, and/or 3) a closing section.

The opening section may be filled in with 1) a list of the discriminative variables and corresponding values that were specified as selection criteria for the cohort, and/or 2) statistics and characteristics of the cohort selected by the selection criteria from the aggregated patient data.

The body section may be filled in with 1) a list of the generated recommendations. Each recommendation may include its metadata (including at least the original pattern p, the outcome o, and the validation table such as, for example, the table 600 of FIG. 6). Recommendations in the body section may be ordered in different ways. In one aspect the user may choose the order. For example, the selected order may be 1) based on decreasing confidence of recommendations, 2) based on decreasing/increasing values of other scores that have been determined/computed (e.g., odds ratio), 3) based on type of recommendations (e.g., descriptive recommendation or imperative recommendations), 4) based on similarity metrics on the prefix of the sequences that generated the recommendations (e.g., example of similarity metric may be a Jaccard Index), and/or 4) based on the semantic types specified by the input terminology.

The closing section may contain a list of all the references used in the recommendations.

The user interface module 552 (e.g., graphical user interface "GUI") may display the generated CPG's (e.g., CPG and metadata 548) to the user (e.g., a domain expert) and enable and allow the domain expert to review a CPG. The "review of a CPG" may include the following actions: 1) changing an order of recommendations in the body section of the CPG, and/or 2) providing/giving feedback on each recommendation. For example, the feedback 560 may include a user flagging a recommendation as wrong/inappropriate, providing/giving a discrete value from 1 to 5 (stars) to a recommendation, where 1 means weak (e.g., very poor/inaccurate), and 5 means strong (e.g., very good/accurate). The feedback 560 information may be used by the recommendation builder module 542 for learning purposes (improve the quality of recommendations that will be generated in the future).

Also, the user interface module 552 enables the user 550 to provide feedback 560 on the CPG to flag a CPG as inappropriate or appropriate. The user may give a discrete value for the CPE from 1 to 5 (e.g., rankings/stars) to a CPG, where 1 means weak (e.g., very poor/inaccurate), and 5 means strong (e.g., very good/accurate). The user interface module 552 enables the user to drill down into the validation tables (e.g., validation table 600 of FIG. 6) and an individual-level or aggregated data for any given recommendation. The user interface module 552 also uses the feedback 560 of the user 550 on both the recommendations and CPG to establish when there is sufficient consensus (e.g., a consensus among domain experts) to consider a CPG as finalized (e.g., a finalized CPG 554). In one aspect, a CPG may be considered finalized (e.g., the finalized CPG 554) when a defined threshold number, majority or defined percentages of users 550 (e.g., domain experts such as, for example, SMEs) have flagged the CPP as appropriate. The threshold number can be configured or learned.

Figure 8:
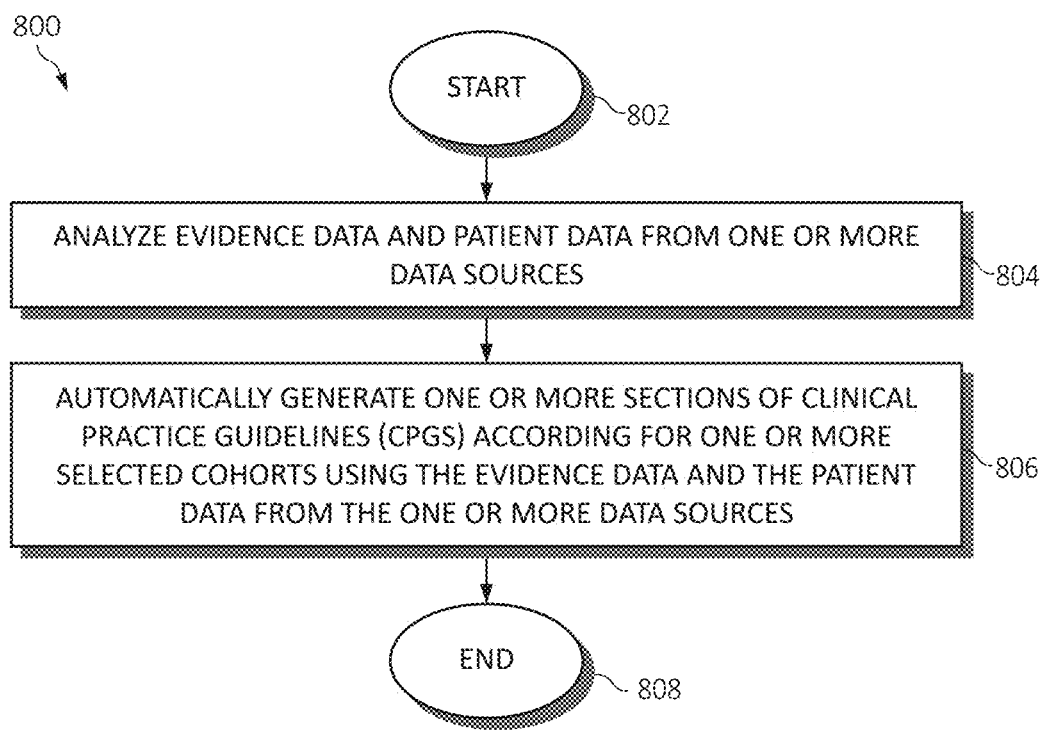
FIG. 8 is a flowchart diagram depicting an additional exemplary method for providing clinical practice guidelines by a processor, again in which aspects of the present invention may be realized.

Turning now to FIG. 8, a method 800 for providing clinical practice guidelines by a processor is depicted, in which various aspects of the illustrated embodiments may be implemented. The functionality 800 may be implemented as a method executed as instructions on a machine, where the instructions are included on at least one computer readable medium or one non-transitory machine-readable storage medium. The functionality 800 may start in block 802.

Evidence data and patient data may be analyzed from one or more data sources, as in block 804. One or more clinical practice guidelines (CPGs) may be automatically generated according for one or more cohorts using the evidence data and the patient data from the one or more data sources, as in block 806. The functionality 800 may end, as in block 808.

In one aspect, in conjunction with and/or as part of at least one block of FIG. 8, the operations of method 800 may include each of the following. The operations of method 800 may analyze the patient data for generating the one or more CPGs. The patient data includes at least health data for a user, social network data, physical conditions of the user, activities of daily living (ADL) and associated context of daily living (CDL) of the user, or a combination thereof. The operations of method 800 may also analyze the evidential data from one or more data sources for generating the one or more CPGs.

The operations of method 800 may assemble the one or more CPGs into a CPG data sources. The operations of method 800 may transform the patient data into one or more statistical patterns enriched with metadata, wherein the metadata data includes one or more outcomes relating to the one or more CPGs and at least one validation table determined from the patient data and the one or more outcomes. The operations of method 800 may select the one or more cohorts according to one or more defined values to filter the patient data. The operations of method 800 may also rank the one or more sections of the one or more CPGs according to a scoring operation.

The operations of method 800 may collect and use feedback data to 1) adjust or apply to the one or more CPG and assist with a machine learning operation, and/or 2) determine a consensus from one or more domain experts relating to the one or more CPGs. The operations of method 800 may initialize a machine learning mechanism to learn and created the one or more CPG.

The present invention may be a system, a method, and/or a computer program product. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, or either source code or object code written in any combination of one or more programming languages, including an object oriented programming language such as Smalltalk, C++ or the like, and conventional procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general-purpose computer, special purpose computer, or other programmable data processing apparatus to produce a machine, such that the instructions, which execute via the processor of the computer or other programmable data processing apparatus, create means for implementing the functions/acts specified in the flowcharts and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowcharts and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowcharts and/or block diagram block or blocks.

The flowcharts and block diagrams in the Figures illustrate the architecture, functionality, and operation of possible implementations of systems, methods, and computer program products according to various embodiments of the present invention. In this regard, each block in the flowcharts or block diagrams may represent a module, segment, or portion of instructions, which comprises one or more executable instructions for implementing the specified logical function(s). In some alternative implementations, the functions noted in the block may occur out of the order noted in the figures. For example, two blocks shown in succession may, in fact, be executed substantially concurrently, or the blocks may sometimes be executed in the reverse order, depending upon the functionality involved. It will also be noted that each block of the block diagrams and/or flowchart illustrations, and combinations of blocks in the block diagrams and/or flowchart illustrations, can be implemented by special purpose hardware-based systems that perform the specified functions or acts or carry out combinations of special purpose hardware and computer instructions.

The invention claimed is:

1. A method for providing clinical practice guidelines by a processor, comprising:
receiving evidence data and patient data from one or more data sources, wherein receiving the evidence data and the patient data includes receiving an input set of cohort selection criteria containing pairs of discriminative variables and corresponding values descriptive of a health-related concept;
executing machine learning logic to generate a cohort model to identify statistically significant patterns and associated outcomes related to one or more cohorts detected in the one or more data sources, wherein identifying the statistically significant patterns and associated outcomes includes filtering the patient data by the discriminative variables and corresponding values using a sequential pattern mining operation to identify the one or more cohorts, and confirming the statistically significant patterns and associated outcomes using a validation table;
querying the evidence data in the one or more data sources using the identified statistically significant patterns and associated outcomes to enrich the statistically significant patterns to enrich and validate the associated outcomes with the evidence data, wherein the querying includes inputting, as the query, a tuple containing information associated with a respective outcome, the tuple including an outcome value, a concept identifier, and a semantic identifier, wherein the concept identifier and the semantic identifier are extracted from a unified medical language system (UMLS), and wherein the validating of the associated outcomes with the evidence data further includes:
identifying a data element in aggregated patient data in the one or more data sources according to the data element containing a same concept identifier and semantic identifier as the respective outcome, wherein, responsive to the query containing input terminology of a hierarchy of concepts, data elements in the aggregated patient data having a parent of the concept identifier of the respective outcome is used, and
building the validation table by determining a number of patients in the aggregated patient data that include a respective pattern and the data element containing the same concept identifier;
automatically generating, by the machine learning logic, one or more clinical practice guidelines (CPGs) having patient recommendations according to the one or more cohorts using information contained on a plurality of templates populated with the evidence data and patient data from the one or more data sources, wherein at least a first of the plurality of templates comprises a first imperative recommendation in which the information describes a first process to achieve a desirable outcome, a second of the plurality of templates comprises a second imperative recommendation in which the information describes a second process leading to an undesirable outcome, and a third of the plurality of templates comprises a descriptive recommendation in which the information links a condition found in one of the one or more cohorts to a condition found in another one of the one or more cohorts;
in conjunction with automatically generating the one or more CPGs, assembling each respective CPG into a document containing a plurality of sections, wherein the plurality of sections include:
an opening section having been populated with at least one of a list of the discriminative variables and corresponding values specified as selection criteria, and statistics and characteristics of the one or more cohorts selected by the input set of cohort selection criteria, a body section having been populated with the patient recommendations, wherein each patient recommendation listed in the body section includes metadata inclusive of an original pattern discovered in the statistically significant patterns and associated outcomes, and the validation table, and a closing section having been populated with a listing of all references used to provide the patient recommendations; and collecting feedback data of an accuracy of the one or more CPGs and using the feedback data to re-train the cohort model to generate optimized CPGs.

2. The method of claim 1, further including:

analyzing the patient data for generating the one or more CPGs, wherein the patient data includes at least health data for a user, social network data, physical conditions of the user, activities of daily living (ADL) and associated context of daily living (CDL) of the user, or a combination thereof; and analyzing the evidence data from one or more data sources for generating the one or more CPGs.

3. The method of claim 1, further including assembling the one or more CPGs into a CPG data source.

4. The method of claim 1, further including transforming the patient data into one or more statistical patterns enriched with the metadata, wherein the metadata data includes one or more outcomes relating to the one or more CPGs and the at least one validation table determined from the patient data and the one or more outcomes.

5. The method of claim 1, further including ranking the one or more sections of one or more CPGs according to a scoring operation.

6. The method of claim 1, wherein collecting the feedback data further includes using the feedback data to determine a consensus from one or more domain experts relating to the one or more CPGs.

7. A system for providing clinical practice guidelines, comprising:

one or more computers with executable instructions that when executed cause the system to:

receive evidence data and patient data from one or more data sources, wherein receiving the evidence data and the patient data includes receiving an input set of cohort selection criteria containing pairs of discriminative variables and corresponding values descriptive of a health-related concept;

execute machine learning logic to generate a cohort model to identify statistically significant patterns and associated outcomes related to one or more cohorts detected in the one or more data sources, wherein identifying the statistically significant patterns and associated outcomes includes filtering the patient data by the discriminative variables and corresponding values using a sequential pattern mining operation to identify the one or more cohorts, and confirming the statistically significant patterns and associated outcomes using a validation table;

query the evidence data in the one or more data sources using the identified statistically significant patterns and associated outcomes to enrich the statistically significant patterns to enrich and validate the associated outcomes with the evidence data, wherein the querying includes inputting, as the query, a tuple containing information associated with a respective outcome, the tuple including an outcome value, a concept identifier, and a semantic identifier, wherein the concept identifier and the semantic identifier are extracted from a unified medical language system (UMLS), and wherein the validating of the associated outcomes with the evidence data further includes:

identifying a data element in aggregated patient data in the one or more data sources according to the data element containing a same concept identifier and semantic identifier as the respective outcome, wherein, responsive to the query containing input terminology of a hierarchy of concepts, data elements in the aggregated patient data having a parent of the concept identifier of the respective outcome is used, and building the validation table by determining a number of patients in the aggregated patient data that include a respective pattern and the data element containing the same concept identifier;

automatically generate, by the machine learning logic, one or more clinical practice guidelines (CPGs) having patient recommendations according to the one or more cohorts using information contained on a plurality of templates populated with the evidence data and patient data from the one or more data sources, wherein at least a first of the plurality of templates comprises a first imperative recommendation in which the information describes a first process to achieve a desirable outcome, a second of the plurality of templates comprises a second imperative recommendation in which the information describes a second process leading to an undesirable outcome, and a third of the plurality of templates comprises a descriptive recommendation in which the information links a condition found in one of the one or more cohorts to a condition found in another one of the one or more cohorts;

in conjunction with automatically generating the one or more CPGs, assemble each respective CPG into a document containing a plurality of sections, wherein the plurality of sections include:

an opening section having been populated with at least one of a list of the discriminative variables and corresponding values specified as selection criteria, and statistics and characteristics of the one or more cohorts selected by the input set of cohort selection criteria, a body section having been populated with the patient recommendations, wherein each patient recommendation listed in the body section includes metadata inclusive of an original pattern discovered in the statistically significant patterns and associated outcomes, and the validation table, and a closing section having been populated with a listing of all references used to provide the patient recommendations; and collect feedback data of an accuracy of the one or more CPGs and using the feedback data to re-train the cohort model to generate optimized CPGs.

8. The system of claim 7, wherein the executable instructions further:

analyze the patient data for generating the one or more CPGs, wherein the patient data includes at least health data for a user, social network data, physical conditions of the user, activities of daily living (ADL) and associated context of daily living (CDL) of the user, or a combination thereof; and analyze the evidence data from one or more data sources for generating the one or more CPGs.

9. The system of claim 7, wherein the executable instructions further assemble the one or more CPGs into a CPG data source.

10. The system of claim 7, wherein the executable instructions further transform the patient data into one or more statistical patterns enriched with the metadata, wherein the metadata data includes one or more outcomes relating to the one or more CPGs and the at least one validation table determined from the patient data and the one or more outcomes.

11. The system of claim 7, wherein the executable instructions further rank one or more sections of the one or more CPGs according to a scoring operation.

12. The system of claim 7, wherein collecting the feedback data further includes using the feedback data to determine a consensus from one or more domain experts relating to the one or more CPGs.

13. A computer program product for providing clinical practice guidelines by a processor, the computer program product comprising a non-transitory computer-readable storage medium having computer-readable program code portions stored therein, the computer-readable program code portions comprising:
   an executable portion that receives evidence data and patient data from one or more data sources, wherein receiving the evidence data and the patient data includes receiving an input set of cohort selection criteria containing pairs of discriminative variables and corresponding values descriptive of a health-related concept;
   an executable portion that executes machine learning logic to generate a cohort model to identify statistically significant patterns and associated outcomes related to one or more cohorts detected in the one or more data sources, wherein identifying the statistically significant patterns and associated outcomes includes filtering the patient data by the discriminative variables and corresponding values using a sequential pattern mining operation to identify the one or more cohorts, and confirming the statistically significant patterns and associated outcomes using a validation table;
   an executable portion that queries the evidence data in the one or more data sources using the identified statistically significant patterns and associated outcomes to enrich the statistically significant patterns to enrich and validate the associated outcomes with the evidence data, wherein the querying includes inputting, as the query, a tuple containing information associated with a respective outcome, the tuple including an outcome value, a concept identifier, and a semantic identifier, wherein the concept identifier and the semantic identifier are extracted from a unified medical language system (UMLS), and wherein the validating of the associated outcomes with the evidence data further includes:
      identifying a data element in aggregated patient data in the one or more data sources according to the data element containing a same concept identifier and semantic identifier as the respective outcome, wherein, responsive to the query containing input terminology of a hierarchy of concepts, data elements in the aggregated patient data having a parent of the concept identifier of the respective outcome is used, and
      building the validation table by determining a number of patients in the aggregated patient data that include a respective pattern and the data element containing the same concept identifier;
   an executable portion that automatically generates, by the machine learning logic, one or more clinical practice guidelines (CPGs) having patient recommendations according to the one or more cohorts using information contained on a plurality of templates populated with the evidence data and patient data from the one or more data sources, wherein at least a first of the plurality of templates comprises a first imperative recommendation in which the information describes a first process to achieve a desirable outcome, a second of the plurality of templates comprises a second imperative recommendation in which the information describes a second process leading to an undesirable outcome, and a third of the plurality of templates comprises a descriptive recommendation in which the information links a condition found in one of the one or more cohorts to a condition found in another one of the one or more cohorts;
   an executable portion that, in conjunction with automatically generating the one or more CPGs, assembling each respective CPG into a document containing a plurality of sections, wherein the plurality of sections include:
   an opening section having been populated with at least one of a list of the discriminative variables and corresponding values specified as selection criteria, and statistics and characteristics of the one or more cohorts selected by the input set of cohort selection criteria,
   a body section having been populated with the patient recommendations, wherein each patient recommendation listed in the body section includes metadata inclusive of an original pattern discovered in the statistically significant patterns and associated outcomes, and the validation table, and
   a closing section having been populated with a listing of all references used to provide the patient recommendations; and
   an executable portion that collects feedback data of an accuracy of the one or more CPGs and using the feedback data to re-train the cohort model to generate optimized CPGs.

14. The computer program product of claim 13, further including an executable portion that:
   analyzes the patient data for generating the one or more CPGs, wherein the patient data includes at least health data for a user, social network data, physical conditions of the user, activities of daily living (ADL) and associated context of daily living (CDL) of the user, or a combination thereof; and
   analyzes the evidence data from one or more data sources for generating the one or more CPGs.

15. The computer program product of claim 13, further including an executable portion that assembles the one or more CPGs into a CPG data source.

16. The computer program product of claim 13, further including an executable portion that transforms the patient data into one or more statistical patterns enriched with the metadata, wherein the metadata data includes one or more outcomes relating to the one or more CPGs and the at least one validation table determined from the patient data and the one or more outcomes.

17. The computer program product of claim 13, further including an executable portion that ranks one or more sections of the one or more CPGs according to a scoring operation.

18. The computer program product of claim 13, wherein collecting the feedback data further includes using the feedback data to determine a consensus from one or more domain experts relating to the one or more CPGs.

* * * * *